United States Patent
Ertel et al.

(10) Patent No.: US 10,631,814 B2
(45) Date of Patent: Apr. 28, 2020

(54) ACQUISITION AND PROCESSING OF MEASUREMENT DATA BY A COMBINED MAGNETIC RESONANCE AND X-RAY DEVICE

(71) Applicants: Dirk Ertel, Forchheim (DE); Yiannis Kyriakou, Spardorf (DE)

(72) Inventors: Dirk Ertel, Forchheim (DE); Yiannis Kyriakou, Spardorf (DE)

(73) Assignee: Siemens Healthcare GmbH, Erlangen (DE)

( * ) Notice: Subject to any disclaimer, the term of this patent is extended or adjusted under 35 U.S.C. 154(b) by 357 days.

(21) Appl. No.: 15/648,892

(22) Filed: Jul. 13, 2017

(65) Prior Publication Data

US 2018/0014805 A1 Jan. 18, 2018

(30) Foreign Application Priority Data

Jul. 13, 2016 (EP) .................... 16179164

(51) Int. Cl.
*A61B 6/00* (2006.01)
*G16H 40/63* (2018.01)
(Continued)

(52) U.S. Cl.
CPC .......... *A61B 6/5247* (2013.01); *A61B 5/0035* (2013.01); *A61B 5/055* (2013.01); *A61B 6/4417* (2013.01); *A61B 6/5264* (2013.01); *A61B 6/541* (2013.01); *G01R 33/4812* (2013.01); *G01R 33/5673* (2013.01); *G06F 19/00* (2013.01); *G06T 7/0012* (2013.01); *G16H 40/63* (2018.01); *A61B 6/486* (2013.01); *A61B 6/5217* (2013.01)

(58) Field of Classification Search
CPC ... A61B 6/5247; A61B 6/5264; A61B 6/4417; A61B 6/5229; A61B 5/0035; A61B 5/055; G01R 33/4808; G01R 33/4812; G01R 33/5673; G06T 7/0012
See application file for complete search history.

(56) References Cited

U.S. PATENT DOCUMENTS

2005/0080333 A1 4/2005 Piron et al.
2009/0306494 A1 12/2009 Scarth et al.
(Continued)

OTHER PUBLICATIONS

European Search Report for related European Application No. 16179164.5 dated Jan. 17, 2017.

*Primary Examiner* — Carolyn A Pehlke
(74) *Attorney, Agent, or Firm* — Lempia Summerfield Katz LLC

(57) ABSTRACT

The acquisition and processing of measurement data by a combined magnetic resonance and X-ray device are provided. Several X-ray images are acquired in succession by a X-ray acquisition unit, and the X-ray images are processed to determine movement data describing a movement of a test subject or at least one region of the test subject during a given time interval. Several data points representing a magnetic resonance signal strength for different phase encodings are acquired by a magnetic resonance acquisition unit during the time interval or an equivalent further time interval, in which the same movement pattern of the test subject or the region is expected. The data points are processed to generate a real space image as a function of the movement data, and/or an acquisition parameter used for the acquisition of at least one of the data points is adjusted as a function of the movement data.

18 Claims, 3 Drawing Sheets

(51) Int. Cl.
*G06T 7/00* (2017.01)
*A61B 5/00* (2006.01)
*A61B 5/055* (2006.01)
*G01R 33/48* (2006.01)
*G01R 33/567* (2006.01)
*G06F 19/00* (2018.01)

(56) References Cited

U.S. PATENT DOCUMENTS

2011/0230755 A1  9/2011  MacFarlane et al.
2012/0093383 A1  4/2012  Claus

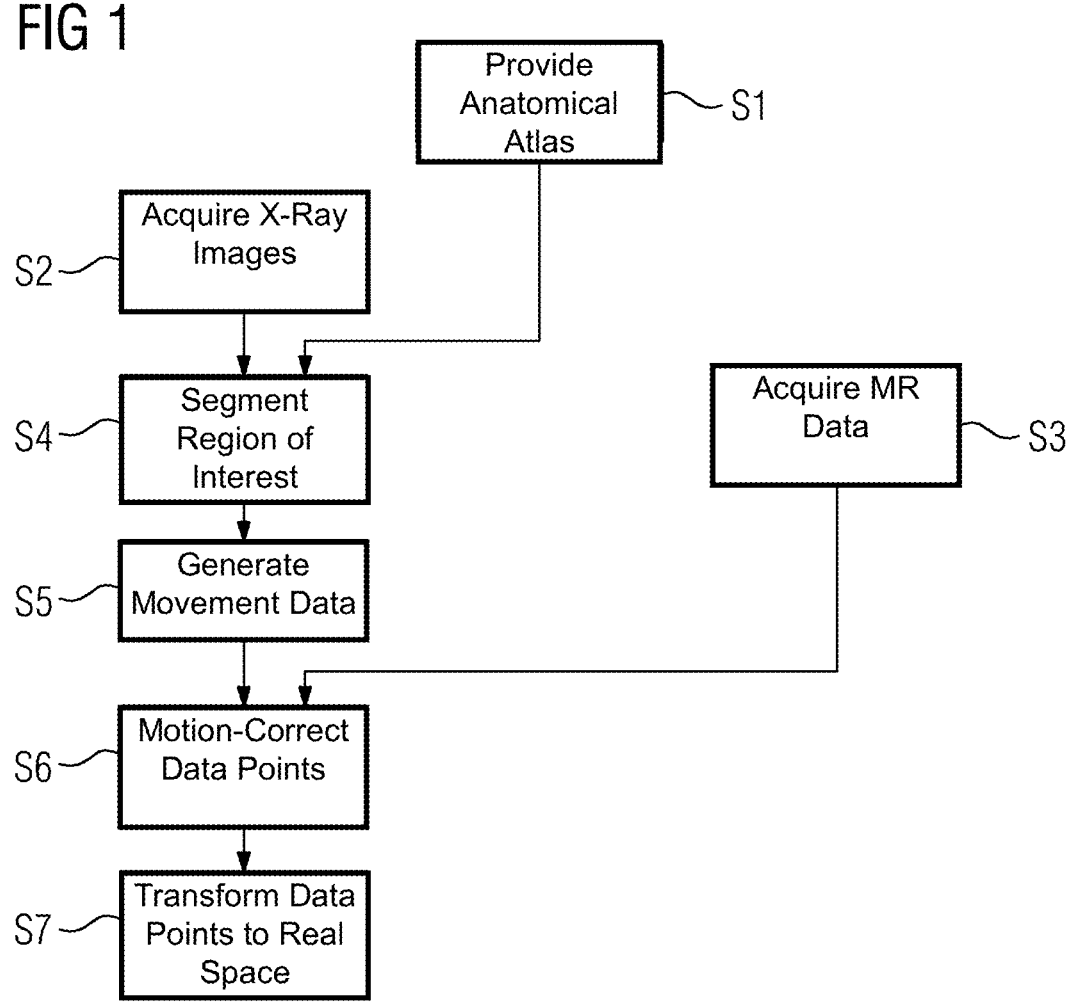

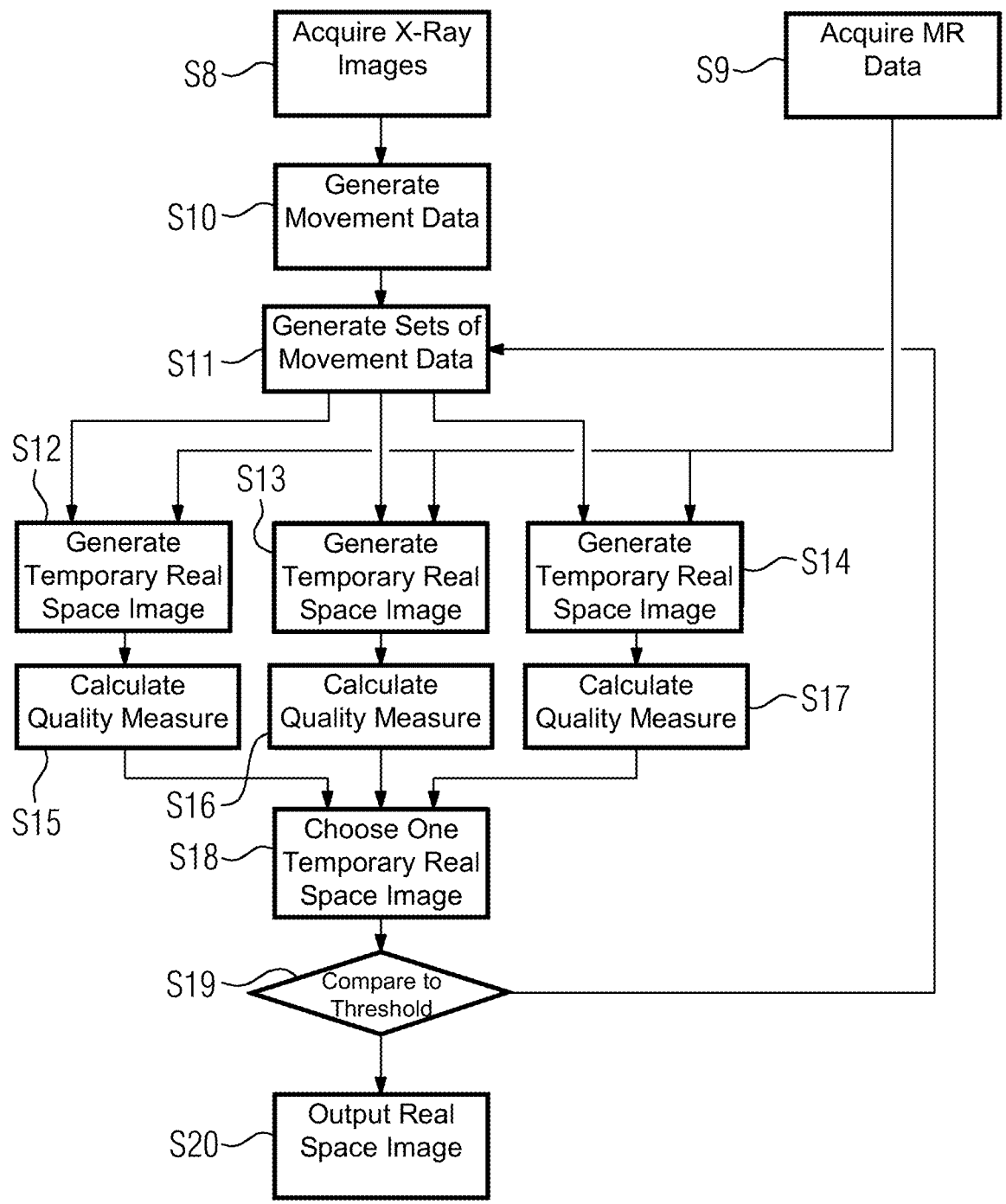

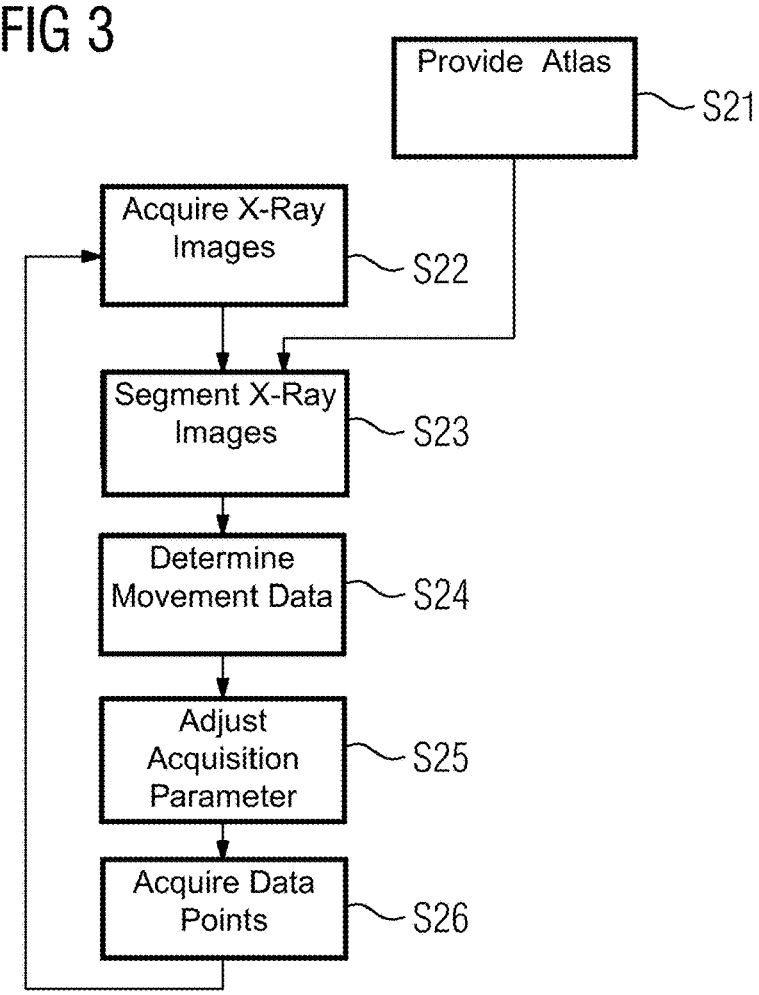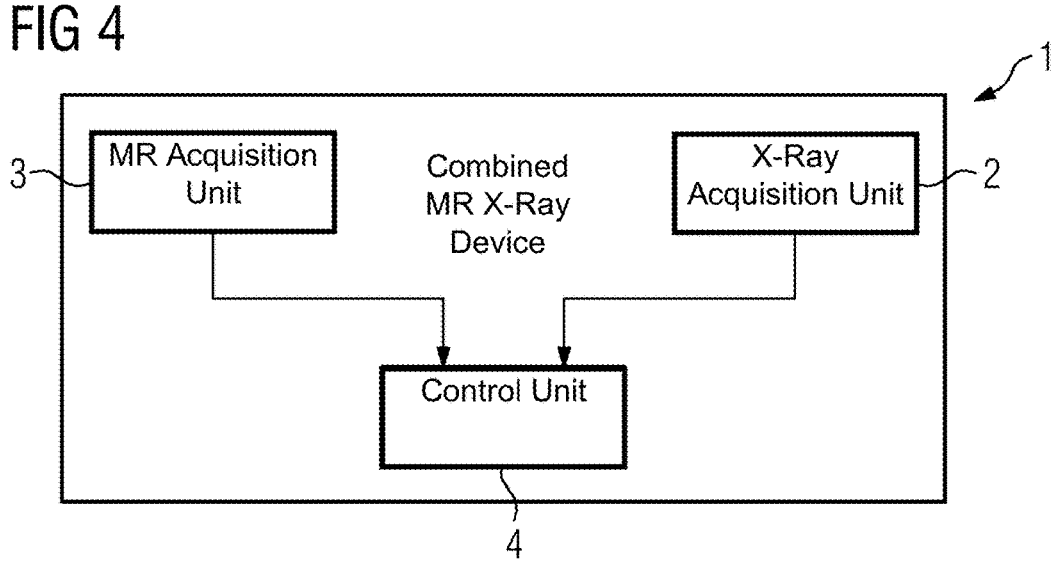

ACQUISITION AND PROCESSING OF MEASUREMENT DATA BY A COMBINED MAGNETIC RESONANCE AND X-RAY DEVICE

This application claims the benefit of EP 16179164.5, filed on Jul. 13, 2016, which is hereby incorporated by reference in its entirety.

BACKGROUND

The present embodiments relate to the acquisition and processing of measurement data by a combined magnetic resonance and X-ray device.

Magnetic resonance imaging is a powerful tool to acquire image data (e.g., in medical imaging). Due to physical and technical constraints, a three dimensional image acquisition in magnetic resonance imaging takes a certain amount of time. The imaging is therefore susceptible to a reduction in image quality and image artefacts due to a movement of a test subject during the image acquisition. This is problematic when living test subjects (e.g., patients) are imaged.

One approach to reduce imaging artefacts due to motion is using an optical tracking of markers that are attached to a test subject. The position of the imaged slice may be adjusted as a function of movement data that is generated by tracking these optical markers. This approach may not be used to track an internal movement of the test subject. This is also a rather laborious approach, since the markers are to be attached to the test subject and there is additional hardware and software used to track these markers.

It is also possible to approximate a movement solely from the acquired magnetic resonance data. For example, an iterative minimization of the entropy of the resulting real space image may be applied. This approach may be useful to compensate for minor movements. Larger movements may hardly be compensated by this approach, since there is no information about the real movement available, and optimization algorithms may get stuck at a local optimum that does not necessarily compensate the real movement.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for the acquisition and processing of magnetic resonance measurement data that provides an improved motion correction is provided.

A method for the acquisition and processing of measurement data by a combined magnetic resonance and X-ray device includes acquiring several X-ray images in succession by a X-ray acquisition unit, and processing the acquired X-ray images to determine movement data describing a movement of a test subject or of at least one region of the test subject during a given time interval. Several data points representing a magnetic resonance signal strength for different phase encodings are acquired by a magnetic resonance acquisition unit during the time interval or an equivalent further time interval, in which a same movement pattern of the test subject or the region is expected. The data points are processed to generate at least one real space image as a function of the movement data, and/or at least one acquisition parameter used for the acquisition of at least one of the data points is adjusted as a function of the movement data.

Movement data derived from X-ray images may be used to compensate a movement during the magnetic resonance data acquisition. X-ray data acquisition may be very fast and may be performed at relatively low dosages when the primary goal of the X-ray acquisition is the acquisition of movement data. It is, for example, known to use X-ray fluoroscopy with a frame rate of 30-60 frames per second at a low radiation dosage. The use of X-ray images for motion correction also allows for an internal movement of the test subject (e.g., the movement of the diaphragm or the heart of a patient) to be compensated. The use of X-ray imaging therefore allows a fast and reliable motion correction. The motion correction may be performed prior or in the process of generating a real space image, and/or acquisition parameters for the acquisition of individual data points for different phase encodings may be adjusted. Since the acquisition and/or the processing of data points for individual phase encodings or a group of a phase encodings is performed as a function of the movement data, movements between individual phase encoding steps may be compensated. Compared to a motion correction applied in real space to the transformed slices acquired by magnetic resonance tomography, imaging artefacts may be reduced, and the image quality may be improved. These improvements are relevant when an undersampling of the k-space is performed (e.g., when using sliding window techniques or other compressed sensing techniques). The described method is also advantageous when real time techniques (e.g., for blood flow imaging) are used.

The movement data may describe a rigid one dimensional or multidimensional movement and therefore a movement with one or multiple degrees of freedom. Additionally or alternatively, the movement data may describe a non-rigid movement (e.g., a deformation of the test subject or the region). The movement data may, for example, describe 1 to 3 translations and/or 1 to 3 rotations of the test subject or the at least one region. The movement data may represent respective individual movements for several regions of the test subject (e.g., separate movement data for a diaphragm and a heart).

The time interval may extend beyond the first and/or the last X-ray image taken in the time interval. It is, for example, possible to first take at least two X-ray images, then acquire a first data point, then acquire a further X-ray image to determine a movement from the previous X-ray image to compensate the movement for the next acquired data point, etc.

The magnetic resonance acquisition unit may be a magnetic resonance tomograph. The magnetic resonance tomograph may include a main coil and several coils to apply gradient fields, as well as antennas for sending and receiving high frequency signals to excite the test subject and receive electromagnetic radiation due to the magnetic resonance from the test subject. The X-ray acquisition unit may include the X-ray source and an X-ray sensor. These components may be attached to a C-arm or may be attached to a component of the magnetic resonance acquisition unit.

The X-ray acquisition unit and the magnetic resonance acquisition unit may be co-registered to a common coordinate system. The test subject may be kept in a constant position with respect to the X-ray acquisition unit and the magnetic resonance acquisition unit for both acquisitions. In one embodiment, the test subject may be fixed to a transfer table that may be moved within the common coordinate system between a first fixed position, in which X-ray data may be acquired by the X-ray acquisition unit, and a second fixed position, in which magnetic resonance data may be acquired by the magnetic resonance acquisition unit.

The motion correction may be applied to individual data points prior to the reconstruction of the real space image, and an uneven sampling of the data space may result. The data space may be a mix between a k-space representing spatial frequencies for some of the spatial directions and/or a real space for the other of the spatial directions. Typically, the direction of a slice-selection is sampled in real space coordinates, while a phase encoding in a direction and/or the sequential recording of several samples while a readout gradient is applied for frequency encoding results in data representing spatial frequencies. To generate a real space image, data representing spatial frequencies may be transformed (e.g., by a Fourier transform). Simple and fast transformations like a discrete Fourier transform use an equal sample spacing in the data space. It is still possible to use these kinds of transforms, when the data space, which may be unevenly sampled after the movement correction, is resampled (e.g., by an interpolation algorithm) to generate equally spaced sample points. In one embodiment, alternative transforms that may handle a data space with unevenly spaced samples may be used.

If the method according to one or more of the present embodiments is used to correct a periodic or a quasi-periodic motion (e.g., the motion of a heart), it is not necessary that the X-ray acquisition and the acquisition of the data points occur during the same time interval. It is, for example, possible to first record the movement by acquiring X-ray images for one or more cycles of the periodic movement, and then record the data points representing the different phase encodings during a different, later cycle or of the movement. The data points may therefore be recorded in an equivalent further time interval, in which the same movement pattern of the test subject or the region is expected as in the time interval during which the X-ray images were acquired. The movements during the time interval and the further time interval are not necessarily identical, but should correspond to the same pattern (e.g., an approximately periodic movement in a certain direction). In this case, the X-ray data and the magnetic resonance data are to be temporally synchronized in some way. If the processing of the data point is performed, after at least a partial cycle of the movement is recorded by a magnetic resonance measurement, this synchronization may be achieved by comparing the X-ray images and a reconstructed approximated real space image of the magnetic resonance data. The approximated real space images may be generated without or with limited motion correction, since the approximated real space images are only used to determine a phase of the movement during the acquisition. Starting from this information, a correlation between the acquisition times of the X-ray images and the data points may be calculated, and a motion correction may be performed as described above. It is, however, also possible to use other sources for the synchronization (e.g., a breath sensor or an EEG-device to synchronize both measurements to a breathing or to a heart cycle of the test subject).

At least a subset of the data points may represent a signal strength at respective coordinates of a common coordinate system, and the processing of the data points may include a collective transformation of these data points to real space to form the real space image. A motion correction step that modifies at least one of the data points and/or respective coordinates of the at least one data point as a function of the movement data is performed prior to the transformation. As previously discussed, the data points are recorded in a mixed data space. Some of the coordinates of the common coordinate system may therefore refer to real space positions, while other coordinates refer to spatial frequencies in the respective direction. The individual data points may also have an associated phase information. This phase information may be recorded by a quadrature detector. Modifying the phase information allows for a correction of a movement by applying an associated phase shift to the respective data point. A movement correction that is applied to the individual data points and therefore to the individual phase encodings and/or individual samples acquired during the application of a frequency encoding gradient does allow for a higher time resolution of the motion compensation than a compensation that only compensates movement in real space after the transformation.

The motion correction may involve a modification of a phase information associated with the data point, where the transform to real space is dependent on the respective phase information of the data points, and/or a shifting of the position of the data point in the common coordinate system and/or a rotation of the data point about the center of the k-space. The center of the k-space is the point corresponding to a spatial frequency of zero. A rotation around the center of the k-space may be equivalent to a rotation about an isocenter of the gradient coils used to scan through the k-space. Since the coordinate of the common coordinate system that corresponds to the direction of a slice selection gradient may be a real space coordinate, a shifting of a data point along this coordinate may be used to compensate a movement in this direction. A shifting of a data point in the direction of a coordinate that encodes spatial frequencies and corresponds to the direction in which a phase encoding or a frequency encoding gradient was applied increases or decreases a recorded spatial frequency in these directions. This kind of motion compensation may be used to compensate for a homogeneous expansion or compression of a region of the test subject. A movement in a direction towards or away from an isocenter of a frequency and/or phase encoding gradient may be compensated by changing the phase information associated with that data point. The amount of the phase shift may be calculated by multiplying the spatial frequency of the respective data point with the motion to be compensated and then multiplying by a phase constant (e.g., by $2\pi$ or $360°$) depending on the convention used for representing the phase.

Motions that may be commonly compensated in medical imaging include the beating of a heart, a breathing motion, and/or a spontaneous rotation of a head. Those motions may be compensated reasonably well by the correction steps mentioned above. Using these corrections is advantageous, since a common transformation of all data points may be used in that case, resulting in a relatively low computational complexity (e.g., by using a discrete Fourier transform). As an alternative, each of the data points may be transformed to real space individually, resulting in "waves" in the real space that may be rotated, translated, and/or deformed to compensate for a movement of the test subject and summed afterwards. While this may allow for more flexible transformations, it also results in a strong increase of the computational demands, especially for high resolution magnetic resonance and data.

The quality of the resulting real space image may be improved by using an iterative approach to the motion correction. In most cases, the movement data generated from X-ray images will not perfectly represent the motion of the test subject. It may therefore be advantageous to use the movement data as a starting point for an optimization process of the image quality. Multiple sets of temporary movement data may be generated by varying the movement data. The data points are processed to generate several temporary real space images as a function of the respective temporary movement data. A measure of the quality of each of the temporary real space images is calculated. One of the temporary real space images is chosen as a function of the respective quality measure. The chosen image is designated as the real space image, or further temporary movement data is generated as a function of the temporary movement data of the chosen image. The generation of the temporary real space image, the selection of a chosen image, and the generation of further temporary movement data are repeated until a stopping condition is met. The measure of quality may be a measure of the entropy of the image or the average information content per pixel of the image. For example, a Shannon entropy may be minimized. The Shannon entropy is defined as the negative sum over the different pixel states. Each summand is the product of the probability of the respective state in the image and the logarithm of that probability. The variation of the movement data and the described optimization may be based on a gradient descent optimization approach.

Alternatively or additionally to the generation of the real space images as a function of the movement data, at least one acquisition parameter may be adjusted as a function of the movement data. A shape of an excitation pulse that is used to excite a magnetic resonance in a selected slice of the test subject and/or the strength of at least one gradient magnetic field used to select the selected slice and/or for frequency encoding and/or for phase encoding may be adjusted as the acquisition parameter. A shape of an excitation pulse may be changed to change the frequency content of the excitation pulse. For example, the central frequency of the excitation pulse and therefore the position of the selected slice may be shifted to compensate a movement. By adjusting the spectral width of the excitation pulse, the excited slice may be compressed or expanded to compensate for a deformation of the test subject. By modifying the strength of the slice selection gradient, the slice that is excited by the excitation pulse may be expanded or compressed. Depending on the position of the slice and the geometric configuration of the gradient selection field, a modification of the gradient strength may also be used to shift the slice that is excited. By modifying the field strength of the frequency encoding gradient, the resulting frequency encoding may be stretched or compressed. As discussed for the slice selection gradient, this may be used to compensate for a compression or expansion of the test subject and, depending on the field geometry used, for compensating for a shift along the direction of frequency encoding.

If a phase encoding is used along several axis of the test subject, a rotation within a plane or a volume, in which a phase encoding occurs, may be achieved by a mixing of the encoding gradients used. The field strength for each encoding direction may be calculated by applying a rotation matrix to the original field strengths. It is also possible to compensate an expansion or a compression of the test subject by varying the duration and/or the field strength of the phase encoding gradient to generate higher or lower spatial frequencies for the phase encoding.

At least one region of the test subject may be chosen. At least one movement parameter describing the movement of that region is determined as a function of the movement data. The data points are processed to generate the real space image as a function of the movement parameter, and/or the acquisition parameter is adjusted as a function of the movement parameter. The determination of the at least one movement parameter for the region results in a motion compensation for that region. Typically one region of interest is chosen (e.g., in the heart, the diaphragm, or the head of the test subject). The motion compensation is parametrized for that region to maximize the image quality in that region. In one embodiment, a movement of multiple regions may be tracked by calculating separate movement parameters for each of these regions, and separate real space images that are optimized to compensate for the motion of the respective region may be generated. For example, one image that is optimally motion compensated for the heart may be generated, and an image that is optimally motion compensated for the diaphragm may be generated. The separate real space images may be optionally combined into a single image, where the individual motion corrected regions are merged.

The region may be segmented as a function of the movement data. Additionally or alternatively, given prior information about the object type of the test subject or the region may be used (e.g., an anatomical atlas).

The processing of the data points to generate the real space image and/or the adjustment of the acquisition parameter for the data point may be performed as a function of at least one further data point acquired previous to the acquisition of the data point, and/or a previous real space image generated as a function of the further data point. A sliding window technique may be used, where a certain defined number of previously acquired data points are used. In one embodiment, a temporary real space image may be generated from undersampled k-space data and the temporary real space image may be used for the adjustment of the acquisition parameter or the processing of the data point.

In the method according to one or more of the present embodiments, the acquisition of at least one of the X-ray images may temporally overlap the acquisition of at least one of the data points, or the acquisition may alternate between an acquisition of least one of the X-ray images and at least one of the data points with no temporal overlap between the two acquisition types. In one embodiment, one or more X-ray images are acquired during the acquisition of each data point or that one or more data points are acquired during the acquisition of each X-ray image. An overlapping or alternating acquisition of X-ray images and data points provides a time synchronization between the X-ray data and therefore the movement data and the magnetic resonance data.

The X-ray images and the data points and timing information describing the relative timing of the acquisition of the X-ray images and the data points may be stored on a storage device, where the generation of the real space image may be performed at a later point in time, after the acquisition of the data points and the X-ray images is complete, based on the stored data. The method according to one or more of the present embodiments may therefore also be used to improve the measurement quality after the measurement is completed.

If the test subject or the region of the test subject move periodically during the time interval and/or the further time interval, the time interval and/or the further time interval may be segmented into time segments as a function of the movement data. The time segments may be grouped according to a respective phase of the periodic movement occurring during the respective time segment, where the real space image is generated as a function of data points acquired during at least two different time segments of the same group. The periodic movement discussed above includes pseudo-periodic movements (e.g., a heartbeat of a patient). Generating the real space image as a function of data points acquired during at least two different time segments of the same group allows an averaging of magnetic resonance data recorded during the same phase of the periodic movement over several cycles of the periodic movement to be used. It is also possible to undersample the k-space during the individual time segments and combine samples for different spatial frequencies from different time segments of the same group to achieve a complete sampling of the k-space.

After the generation of the real space image, a condition that depends on the movement data and the real space image and prior knowledge of the test subject or the region may be evaluated. A user of the combined magnetic resonance and X-ray device is informed when the condition is fulfilled. The prior knowledge may concern certain features that may be recognized in the real space image and certain features that may be recognized in the movement data. The condition may determine if the real space image and/or the movement data show a sufficiently strong deviation from the expected data that may indicate a problem of the test subject (e.g., a health problem of a patient) or a problem in the measurement procedure. The user may therefore be notified to take special note of the features in the real space image and/or the movement data that may indicate a problem and/or may be relevant for determining a status of the test subject. For example, the shape of a heart in the real space image and a movement pattern of the heart may be automatically analyzed, and the user may be notified if there is a sufficient deviation from the expected features. The user's attention is therefore focussed on potentially relevant features.

In addition to the method discussed above, one or more of the present embodiments concern a combined magnetic resonance and X-ray device including an X-ray acquisition unit, a magnetic resonance acquisition unit, and a control unit. The X-ray acquisition unit and the magnetic resonance acquisition unit are controllable, and the real space image is generatable by the control unit according to the method discussed above and below.

One or more of the present embodiments also concern a computer program product including a program. The computer program product (e.g., the program) is directly loadable into a memory unit of the control unit of a combined magnetic resonance and X-ray device, to execute the method discussed above and below, when the program is executed in the control unit of the combined magnetic resonance and X-ray device.

Additionally, one or more of the present embodiments concern an electronically readable data storage medium (e.g., a non-transitory computer-readable storage medium) including control information (e.g., instructions) stored thereon allowing the execution of the method discussed above and below when the control information is executed on a control unit of the combined magnetic resonance and X-ray device.

BRIEF DESCRIPTION OF THE DRAWINGS

FIGS. 1-3 show flow charts of different exemplary embodiments of a method for the acquisition and processing of measurement data by a combined magnetic resonance and X-ray device; and FIG. 4 shows an exemplary embodiment of a combined magnetic resonance and X-ray device.

DETAILED DESCRIPTION

FIG. 1 shows one embodiment of a method for the acquisition and a processing of measurement data by a combined magnetic resonance and X-ray device. In act S1, prior knowledge about the test subject is provided in the form of an anatomical atlas that will be used later in the method to determine relevant regions (e.g., a heart), for which a movement correction may be provided.

In act S2, a plurality of X-ray images are acquired in succession by a X-ray acquisition unit. During the same time interval, in which the X-ray images are acquired, several data points representing a magnetic resonance signal strength for different phase encodings are acquired by a magnetic resonance acquisition unit during act S3. The acquisition of the different data points is done according to the prior art in magnetic resonance imaging. A certain slice of the test subject is excited by an excitation pulse, a phase encoding gradient is applied to provide a phase encoding, and the radiation due to the decay of the magnetic resonance is measured while a frequency encoding gradient is applied. To convert the spatial frequencies measured due to the frequency and phase encoding into real space, a Fourier transform is applied to the resulting signals. Multiple data points may be recovered for each of the different phase encodings. Each of these data points corresponds to a different spatial frequency in the direction of the frequency encoding gradient. In one embodiment, the test subject or certain regions of the test subject move during the time interval between the recording of the data points, which may reduce the resulting image quality and/or create imaging artefacts. In the described method, the X-ray images are therefore used to determine the movement of the test subject and/or a specific region of the test subject and to provide motion correction for the acquired data points, as described below.

To allow the usage of the X-ray images for the correction of the data points, it is to be provided that the recording of the X-ray images and the data points is temporally correlated. This may be achieved by using an overlapping acquisition, where the acquisition of one or more X-ray images overlaps the time used to record a data point or vice versa. The X-ray acquisition unit and the magnetic resonance acquisition unit may therefore be operated simultaneously. In an alternative embodiment, the different data acquisitions may be interleaved. One or more X-ray images may be acquired; after, one or more data points may be acquired, and the process may be repeated starting with the acquisition of X-ray images. In both of these cases, there is a close temporal correlation between the acquisition of the X-ray images and the magnetic resonance data points. In another alternative embodiment, a known periodicity of an observed movement (e.g., the regularity of a heartbeat or a breathing pattern) may be used to correlate X-ray images that are acquired in one time interval with magnetic resonance data points acquired during a further time interval. The acquisitions may be synchronized by using a trigger signal (e.g., derived from an EEG or a breathing sensor).

In act S4, a region of interest is segmented in the X-ray images recorded in act S2. To achieve this, the X-ray images may be elastically registered to the anatomical atlas provided in act S1. Additionally or alternatively, a movement between the individual X-ray images may be used to segment a region of interest. In this case, the movement detection that will be described for act S5 may already be performed in act S4.

In act S5, movement data describing a movement of the region segmented in act S4 is generated. The movement may be detected, for example, by using an optical flow method and/or by using a feature detection in the X-ray images and by tracking these features through the X-ray images acquired in sequence. Methods for motion determination from images (e.g., X-ray images) are well known in the state of the art and will not be described in detail.

From this general movement data, specific movement parameters describing the movement of the region determined in act S4 are determined in act S5. Such movement parameters may describe a translation and/or a rotation of the region in 1 to 3 dimensions and/or a compression and/or an expansion of the region.

The movement parameters determined in act S5 are used in the correction act S6 to modify the data points recorded in act S3. The data points represent a signal strength at respective coordinates of a common coordinate system. The common coordinate system has one or more coordinates that represent spatial frequencies in the respective directions of a phase and/or a frequency encoding. The common coordinate system may also provide one or more coordinates that are associated with a position in real space in the respective direction. This direction may be the direction of a slice selection.

To correct for the detected motion, the individual data points and/or the respective coordinates are modified as a function of the movement data (e.g., the movement parameters determined in act S5). Since the common coordinate system represents a data space, where some of the coordinates are real space coordinates and some of the coordinates are k-space coordinates, the kind of transformation used for motion compensation depends on the type of coordinate modified. The motion correction may involve a modification of a phase information associated with the data point, where a later transformation of the data points to real space is dependent on the respective phase information. A modification of phase information that is associated with a k-space coordinate is equivalent to a shift of a position in this direction. If, for example, all phases of all data points would be shifted by a respective value that is proportional to the product of the respective spatial frequency represented by this data point and the displacement distance, this would be equivalent to shifting the real space image by this distance after the transformation to real space.

If a motion along a real space coordinate of the common coordinate system may be compensated, the respective coordinate of the data point may simply be changed by that amount. Rotations may be compensated if the rotation is confined to a plane spanned by two real space coordinates and/or if the plane of rotation is spanned by two k-space coordinates and therefore by two phase and/or frequency encoding directions and the axis of rotation is the isocentre of the magnetic resonance acquisition.

After the individual data points are motion corrected in act S6, the data points are jointly transformed to real space in act S7, resulting in the real space image.

If the interval in which data is recorded in the acts S2 and S3 is sufficiently long to, for example, record multiple three dimensional magnetic resonance images, different subgroups of the data points may be transformed separately to form separate real space images. Alternatively, the time interval for recording data in the acts S2 and S3 may be chosen to be rather short, such that only one or a few data points are recorded in act S3. The acts S2 to S7 may be performed repeatedly in this case. The acts S6 and S7 may be performed each time that sufficient data was acquired for the reconstruction of a real space image. In one embodiment, sliding window or other undersampling techniques may be used. For example, only one or a few additional data points may be recorded in act S3 for each new transformation to real space in act S7 and merged with data points recorded in previous iterations to allow for a high quality near real time reconstruction.

The correction of individual data points in act S6 may lead to an uneven sampling of the mixed k- and real space. To allow for an easy and fast transformation into real space in act S7, the mixed k- and real space of the common coordinate system may be resampled (e.g., by an interpolation algorithm).

In an alternative embodiment, a real space image and/or data points of a previous loop of the method may be used to determine the movement data in act S5.

The method shown in FIG. 1 may be split into an acquisition part, containing the acts S2 and S3, and a processing part, containing the further acts. The acquisition part may be performed separately from the processing part. The X-ray images acquired in act S2, the data points acquired in act S3, and timing information describing the relative timing of the acquisitions may, for example, be recorded to a storage device. This data may be used at a later point in time and may be processed as described above.

If a periodic movement is observed, the periodicity may be used to improve the image quality. For example, the time interval, during which data is acquired in acts S2 and S3, may be segmented into time segments as a function of the movement data or the movement parameters. The segments may be grouped according to a respective phase of the periodic movement occurring during the respective time segment. The respective phase may be determined, for example, from the movement parameter determined from the current X-ray image. The real space image may be generated in act S7 as a function of data points acquired during at least two different time segments of the same group.

FIG. 2 shows a further embodiment of a method for the acquisition and processing of measurement data by a combined magnetic resonance and X-ray device. The acts S8 and S9 are equivalent to the acts S2 and S3, where X-ray images and magnetic resonance data points are acquired. In act S10, movement data is generated from the X-ray images acquired in act S8. This may be performed, as described, to the acts S1, S4, and S5 in FIG. 1 or by directly applying a motion detection.

In act S11, multiple sets of movement data is generated by varying the movement data determined in act S10. To keep the example simple, only one degree of freedom of motion is considered in FIG. 2. The different sets of movement data will represent one set of movement data that is identical to the movement data generated in act S10, one set showing a slightly stronger movement, and one set showing a slightly weaker movement. Typically, several degrees of a movement may be varied. The variation may be limited to two alternatives, or more than three alternatives may be generated for each degree of freedom.

In acts S12 to S14, several temporary real space images are generated as a function of the respective temporary movement data generated in act S11. The generation of the real space images is performed as described for acts S6 and S7 in FIG. 1. In acts S15 to S17, a measure for the quality of each of the temporary real space images is calculated. For example, a Shannon entropy for each of the temporary real space images may be calculated.

In act S18, one of the temporary real space images is chosen (e.g., the temporary real space image with the lowest Shannon entropy). The measure for the quality of the chosen image is compared to a threshold value in act S19. If the measure for the quality of the chosen image is higher than the threshold value, the process is repeated starting from act S11. Instead of the movement data generated in act S10, the temporary movement data of the chosen image is used in act S11. If the measurement of quality is sufficiently low, the method proceeds to act S20, where the chosen image is output as the real space image.

The previous examples have shown a correction of the data point to compensate a movement after the acquisition of the individual data points. Additionally or alternatively, the movement may be compensated by adjusting acquisition parameters used during the acquisition of the data points. An example for this procedure is shown in FIG. 3. The acts S21, S22, S23, and S24 are equivalent to the acts S1, S2, S4, and S5 as described with respect to FIG. 1. In act S21, an atlas is provided; in act S22, one or several X-ray images are acquired; in act S23, the X-ray images are segmented via the atlas provided in act S21; and in act S24, movement data (e.g., motion parameters that describe the movement of a region of a test subject) are determined. The movement parameters determined in act S24 are used in act S25 to adjust at least one acquisition parameter for the acquisition of at least one data point in act S26. A movement in the direction of the slice selection gradient may be compensated by adjusting the shape of the excitation pulse (e.g., by shifting a center frequency and/or by adjusting the strength of a slice selection gradient). An adjustment of the strength of the frequency encoding gradient or the strength of a phase encoding gradient may be used to compensate a compression or expansion of the region of the test subject in the respective direction. Depending on the field geometry, adjusting the phase encoding gradient and/or the frequency encoding gradient may also be used to compensate for a translation of the test subject or the region in the respective direction.

After one or several data points are acquired in act S26 with the acquisition parameters that were adjusted in act S25, the procedure is repeated from act S22, until all required data points are assembled. The data points may either be transformed to real space directly, or additional corrections, as described with reference to FIG. 1 or FIG. 2, may be applied.

FIG. 4 shows one embodiment of a combined magnetic resonance X-ray device 1 including an X-ray acquisition unit 2, a magnetic resonance acquisition unit 3, and a control unit 4 (e.g., a controller). The X-ray acquisition unit 2 and the magnetic resonance acquisition unit 3 are controllable by the control unit 4 to acquire X-ray images and magnetic resonance data points, as described above. The control unit 4 may also adjust the acquisition parameters for the acquisition of the data points as a function of the movement data, as described with respect to FIG. 3, and processes the data points to generate at least one real space image, as described with respect to FIGS. 1 and 2.

The described method may also be provided in the form of a computer program product (e.g., including a non-transitory computer-readable storage medium) that may implement the method on the control unit 4 when the computer program product is executed on the control unit 4. In another embodiment, a non-transitory computer-readable storage medium (e.g., an electronically readable data storage unit) may include control information (e.g., instructions) stored thereon. The non-transitory computer-readable storage medium may include a computer software product and allows the execution of the described method when the instructions are executed on the control unit 4 of the combined magnetic resonance and X-ray device 1.

Although the present invention has been described in detail with reference to exemplary embodiments, the present invention is not limited by the disclosed examples from which the skilled person is able to derive other variations without departing from the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for acquisition and processing of measurement data by a combined magnetic resonance and X-ray device, the method comprising:
   acquiring, by an X-ray device, a plurality of X-ray images in succession; and
   determining, by an X-ray device, movement data describing a movement of a test subject or at least one region of the test subject during a given time interval, the determining of the movement data comprising processing the plurality of X-ray images;
   acquiring, by a magnetic resonance device, a plurality of data points representing a magnetic resonance signal strength for different phase encodings during the given time interval or an equivalent further time interval, a same movement pattern of the test subject or the at least one region being expected for the equivalent further time interval compared to the given time interval; and
   generating at least one real space image as a function of the movement data, wherein generating the at least one real space image comprises processing the plurality of data points,
   adjusting at least one acquisition parameter used for the acquisition of at least one data point of the plurality of data points acquired by the magnetic resonance device as a function of the movement data, or
   generating the at least one real space image as a function of the movement data, wherein generating the at least one real space image comprises processing the plurality of data points, and adjusting the at least one acquisition parameter used for the acquisition of the at least one data point of the plurality of data points as a function of the movement data.

2. The method of claim 1, wherein at least a subset of data of the plurality of data points represents a signal strength at respective coordinates of a common coordinate system, and the processing of the plurality of data points includes a collective transformation of the subset of data to real space to form the real space image, and
   wherein the method further comprises performing, prior to the collective transformation, a motion correction that modifies at least one data point of the plurality of data points, coordinates of the respective data point, or the at least one data point and the coordinates as a function of the movement data.

3. The method of claim 2, wherein the motion correction includes a modification of phase information associated with the at least one data point, and
wherein the collective transformation to real space is dependent on the respective phase information of the data points, a shifting of a position of the data point in the common coordinate system, a rotation of the data point about a center of a k-space, or any combination thereof.

4. The method of claim 1, further comprising:
generating multiple sets of temporary movement data, the generating of the multiple sets of temporary movement data comprising varying the movement data;
generating a plurality of temporary real space images as a function of the respective temporary movement data, the generating of the plurality of temporary real space images processing the plurality of data points;
calculating a measure for a quality of each temporary real space image of the plurality of temporary real space images;
selecting one temporary real space image of the plurality of temporary real space images as a function of the respective quality measure;
designating the selected temporary real space image as the real space image or generating further temporary movement data as a function of the temporary movement data of the selected image; and
repeating the generation of the plurality of temporary real space images, the selection of the one temporary real space image, and the generation of further temporary movement data until a stopping condition is met.

5. The method of claim 1, wherein a shape of an excitation pulse that is used to excite a magnetic resonance in a selected slice of the test subject, a strength of at least one gradient magnetic field used to select the selected slice, for frequency encoding, for phase encoding, or any combination thereof is adjusted as the acquisition parameter.

6. The method of claim 1, further comprising:
selecting the at least one region of the test subject;
determining at least one movement parameter describing the movement of the at least one region of the test subject as a function of the movement data;
generating the real space image as a function of the movement parameter, the generating of the real space image processing the plurality of data points, adjusting the acquisition parameter as a function of the movement parameter, or a combination thereof.

7. The method of claim 5, wherein the at least one region is segmented as a function of the movement data.

8. The method of claim 1, wherein generating the at least one real space image, adjusting the at least one acquisition parameter for the at least one data point, or a combination thereof is performed as a function of at least one further data point, the at least one further data point being acquired previous to the acquisition of the data point, as a function of a previous real space image generated as a function of the further data point, or as a function of a combination thereof.

9. The method of claim 1, wherein the acquisition of at least one X-ray image of the plurality of X-ray images temporally overlaps the acquisition of at least one data point of the plurality of data points, or
wherein the acquisition of the at least one X-ray image and the acquisition of the at least one data point alternates between the acquisition of the at least one X-ray image and the acquisition of the at least one data point with no temporal overlap.

10. The method of claim 1, wherein the plurality of X-ray images, the plurality of data points, and a timing information describing a relative timing of the acquisition of the plurality of X-ray images and the plurality of data points are stored on a storage device, and
wherein the generation of the at least one real space image is performed at a later point in time, after the acquisition of the plurality of data points and the acquisition of the plurality of X-ray images is complete, based on the stored data.

11. The method of claim 1, wherein the test subject or a region of the test subject moves periodically during the time interval, the further time interval, or the time interval and the further time interval,
wherein the time interval, the further time interval, or the time interval and the further time interval are segmented into time segments as a function of the movement data,
wherein the time segments are grouped according to a respective phase of the periodic movement occurring during the respective time segment, and
wherein the at least one real space image is generated as a function of data points of the plurality of data points acquired during at least two different time segments of the same group.

12. The method of claim 1, further comprising:
evaluating, after the generation of the at least one real space image, a condition that depends on the movement data and the at least one real space image, and prior knowledge of the test subject or the at least one region; and
informing a user of the combined magnetic resonance and X-ray device when the condition is fulfilled.

13. A combined magnetic resonance and X-ray device comprising:
an X-ray acquisition device;
a magnetic resonance acquisition device; and
a controller,
wherein the X-ray acquisition device and the magnetic resonance acquisition device are controllable and a real space image is generatable by the control unit, the generation of the real space image, by the control unit, comprising:
acquisition, by the X-ray device, of a plurality of X-ray images in succession and determination of movement data describing a movement of a test subject or at least one region of the test subject during a given time interval, the determination of the movement data comprising processing of the plurality of X-ray images;
acquisition, by the magnetic resonance device, of a plurality of data points representing a magnetic resonance signal strength for different phase encodings during the given time interval or an equivalent further time interval, a same movement pattern of the test subject or the at least one region being expected for the equivalent further time interval compared to the given time interval; and
generation of the real space image as a function of the movement data, wherein generation of the real space image comprises processing the plurality of data points, adjustment of at least one acquisition parameter used for the acquisition of at least one data point of the plurality of data points acquired by the magnetic resonance device as a function of the movement data, or generation of the real space image as a function of the movement data, wherein generation of the real space image comprises processing the plurality of data points, and adjustment of the at least one acquisition parameter used for the acquisition of the at least further one data point of the plurality of data points as a function of the movement data.

14. A computer program product comprising a non-transitory computer-readable storage medium storing a program having instructions, the program being directly loadable into a memory unit of a controller of a combined magnetic resonance and X-ray device and the instructions being executable by the controller to acquire and process measurement data, the instructions comprising:

acquiring, by an X-ray device, a plurality of X-ray images in succession and determining movement data describing a movement of a test subject or at least one region of the test subject during a given time interval, the determining of the movement data comprising processing the plurality of X-ray images;

acquiring, by a magnetic resonance device, a plurality of data points representing a magnetic resonance signal strength for different phase encodings during the given time interval or an equivalent further time interval, a same movement pattern of the test subject or the at least one region being expected for the equivalent further time interval compared to the given time interval; and generating at least one real space image as a function of the movement data, wherein generating the at least one real space image comprises processing the plurality of data points, adjusting at least one acquisition parameter used for the acquisition of at least one data point of the plurality of data points acquired by the magnetic resonance device as a function of the movement data, or generating the at least one real space image as a function of the movement data, wherein generating the at least one real space image comprises processing the plurality of data points, and adjusting the at least one acquisition parameter used for the acquisition of the at least one data point of the plurality of data points as a function of the movement data.

15. A non-transitory computer-readable storage medium storing instructions executable by a controller of a combined magnetic resonance and X-ray device to acquire and process measurement data, the instructions comprising:

acquiring, by an X-ray device, a plurality of X-ray images in succession and determining movement data describing a movement of a test subject or at least one region of the test subject during a given time interval, the determining of the movement data comprising processing the plurality of X-ray images;

acquiring, by a magnetic resonance device, a plurality of data points representing a magnetic resonance signal strength for different phase encodings during the given time interval or an equivalent further time interval, a same movement pattern of the test subject or the at least one region being expected for the equivalent further time interval compared to the given time interval; and generating at least one real space image as a function of the movement data, wherein generating the at least one real space image comprises processing the plurality of data points, adjusting at least one acquisition parameter used for the acquisition of at least one data point of the plurality of data points acquired by the magnetic resonance device as a function of the movement data, or generating at least one real space image as a function of the movement data, wherein generating the at least one real space image comprises processing the plurality of data point, and adjusting the at least one acquisition parameter used for the acquisition of the at least one data point of the plurality of data points as a function of the movement data.

16. The non-transitory computer-readable storage medium of claim 15, wherein at least a subset of data of the plurality of data points represents a signal strength at respective coordinates of a common coordinate system, and the processing of the plurality of data points includes a collective transformation of the subset of data to real space to form the real space image, and wherein the instructions further comprise performing, prior to the collective transformation, a motion correction that modifies at least one data point of the plurality of data points, coordinates of the respective data point, or the at least one data point and the coordinates as a function of the movement data.

17. The non-transitory computer-readable storage medium of claim 16, wherein the motion correction includes a modification of phase information associated with the at least one data point, and wherein the collective transformation to real space is dependent on the respective phase information of the data points, a shifting of a position of the data point in the common coordinate system, a rotation of the data point about a center of a k-space, or any combination thereof.

18. The non-transitory computer-readable storage medium of claim 15, wherein the instructions further comprise:

generating multiple sets of temporary movement data, the generating of the multiple sets of temporary movement data comprising varying the movement data;

generating a plurality of temporary real space images as a function of the respective temporary movement data, the generating of the plurality of temporary real space images comprising processing the plurality of data points;

calculating a measure for a quality of each temporary real space image of the plurality of temporary real space images;

selecting one temporary real space image of the plurality of temporary real space images as a function of the respective quality measure;

designating the selected temporary real space image as the real space image or generating further temporary movement data as a function of the temporary movement data of the selected image; and repeating the generation of the plurality of temporary real space images, the selection of the one temporary real space image, and the generation of further temporary movement data until a stopping condition is met.

* * * * *